(12) United States Patent
Jones

(10) Patent No.: US 9,492,307 B1
(45) Date of Patent: Nov. 15, 2016

(54) SUPPORT AND STABILIZATION DEVICE FOR DIALYSIS TREATMENT

(76) Inventor: Elizabeth J. Jones, Tamarac, FL (US)

(*) Notice: Subject to any disclaimer, the term of this patent is extended or adjusted under 35 U.S.C. 154(b) by 75 days.

(21) Appl. No.: 13/609,458

(22) Filed: Sep. 11, 2012

(51) Int. Cl.
*A61F 5/37* (2006.01)

(52) U.S. Cl.
CPC ........................................ *A61F 5/37* (2013.01)

(58) Field of Classification Search
CPC .......................................................... A61F 5/37
USPC ..................... 5/646, 647; 2/69; 128/878, 875
See application file for complete search history.

(56) References Cited

U.S. PATENT DOCUMENTS

| | | | |
|---|---|---|---|
| 3,547,112 A | * | 12/1970 | Courtney .................. A61F 5/10 128/DIG. 15 |
| 5,485,856 A | * | 1/1996 | Buckland .......................... 5/647 |
| 6,817,032 B2 | * | 11/2004 | Hollander ........................... 2/69 |
| 2004/0000002 A1 | * | 1/2004 | Hollander ........................... 2/69 |
| 2006/0053524 A1 | * | 3/2006 | Hollander ........................... 2/69 |
| 2012/0060280 A1 | * | 3/2012 | Kelly et al. ...................... 5/490 |
| 2012/0152261 A1 | * | 6/2012 | O'Connor et al. ........... 128/878 |

* cited by examiner

*Primary Examiner* — Fredrick Conley
(74) *Attorney, Agent, or Firm* — The Keys Law Firm PLLC

(57) ABSTRACT

A support and stabilization device for use by patients receiving dialysis comprising modified stabilization glove and a modified support pillow. The stabilization glove is a conventional glove styled hand covering that has a plurality of hook-and-loop fasteners, specifically loop component fastener strips permanently affixed to its palmar side. The modified support pillow is a traditional pillow with an elongated body having fabric outer cover and a removable waterproof inner portion. Opposing hook component fastener strips are permanently affixed to the top surface of the support pillow. As a result, when the opposing fasteners engage a removable attachment between the pillow and glove is created that does not physically restrain the patient in an inappropriate or undesirable manner.

14 Claims, 4 Drawing Sheets

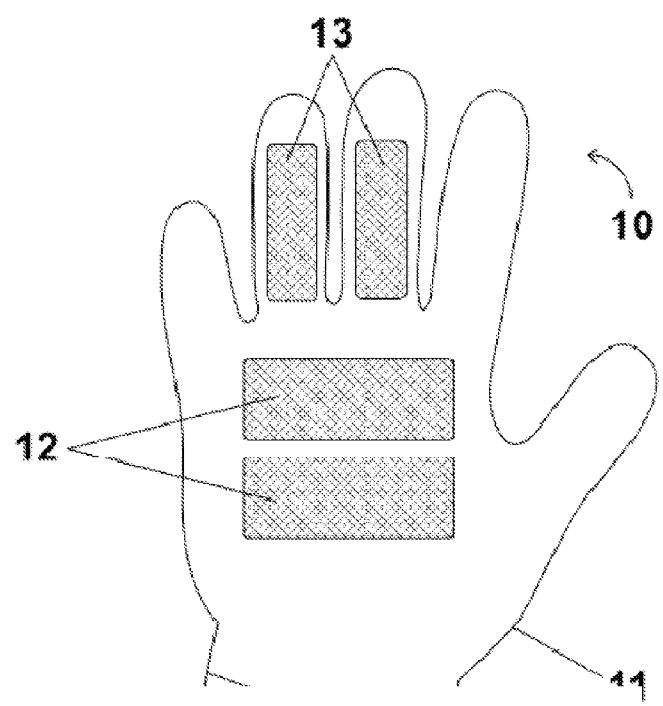
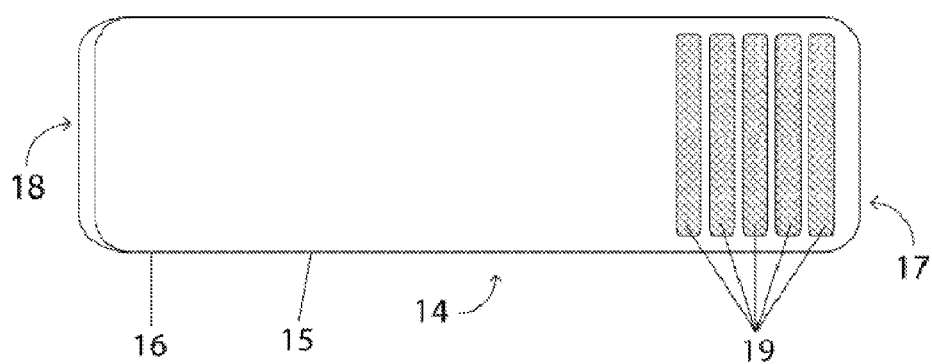

SUPPORT AND STABILIZATION DEVICE FOR DIALYSIS TREATMENT

BACKGROUND OF THE INVENTION

1. Field of the Invention

This invention relates to a dialysis comfort product that provides a supportive structure and a stabilization mechanism for the arm of a patient receiving dialysis.

2. Description of the Prior Art

In humans, kidneys have an important role in maintaining health. Two of the most prominent roles of the kidneys are to filter waste products from the blood and regulate body fluid balance. Individuals can experience varying levels of issues with their kidney function. These issues can range from acute kidney failure, which can usually improve, to chronic kidney failure, which is typically permanent. In the case of either issue, dialysis may be used to perform some of the function of the individual's impaired kidneys. In the United States, there are over 200,000 people who receive some form of dialysis on an ongoing basis. For people with acute kidney failure, dialysis is received until the kidneys get better. In the case of chronic kidney failure, however, dialysis may be required for the rest of the individual's life or otherwise until a renal transplant can be performed.

There are two types of dialysis treatments, hemodialysis and peritoneal dialysis. In hemodialysis, a dialysis machine is connected to the person receiving treatment such that their blood can flow out of their body, through a filter in the dialysis machine, and back into their body. The filter, or dialyzer, acts as an artificial kidney and filters the person's blood as it passes through the hemodialyzer to rid their body of harmful wastes, extra salt and water. By performing such actions, hemodialysis treatment helps keep the body in balance. Hemodialysis treatment, however, will often require the person receiving said treatment to spend around four hours connected to the dialysis machine, on multiple occasions each week.

The use of products and devices to provide comfort to a patient receiving hemodialysis, or dialysis comfort products, is well known. Items such as recliner chairs, catheter covers, and various clothing garments to improve patient comfort are well known in the art. In addition, fabric straps designed to secure and stabilize dialysis/infusion tubing during patient treatment are an available option to assist in the stabilization of treatment tubing and to minimize tugging and painful infiltration.

A constraint on any product or device designed for dialysis patients is that in most settings, it is inappropriate or undesirable for a patient to be physically restrained for the purpose of adding stability. As physical restraints are not generally used, a patient may inadvertently or unconsciously move the arm receiving treatment and cause pain or discomfort. As dialysis patients are often receiving treatments for relatively long periods of time, inadvertent or unconscious movement can be common where a patient falls asleep or overlooks the device connected to them and then moves in an undesirable manner. Similarly, being seated for such a long period will often result in the patient's hand becoming cold due to diminished blood flow or arm being uncomfortable due to lack of support.

The Applicant's invention described herein provides for a support and stabilization device for providing the arm of a dialysis patient a supportive structure and a stabilization mechanism without restraining the patient's arm. The support and stabilization device includes a modified elongated pillow with an accompanying hand covering, with each having opposing fasteners on their respective exterior that can removably engage with each other. The opposing fasteners are positioned on the pillow and hand covering such that a patient can allow the arm receiving dialysis treatment to rest naturally and comfortably with the fasteners engaged so that the arm only moves as a result of conscious and deliberate action by the patient.

SUMMARY OF THE INVENTION

A support and stabilization device for use by patients receiving dialysis comprising modified stabilization glove and a modified support pillow. The stabilization glove is a conventional glove styled hand covering and is defined by the presence of a plurality of Velcro® fasteners permanently affixed to the palmar side of the stabilization glove. Four loop component fastener strips are used; two (2) affixed to the upper palm area of the stabilization glove and two (2) affixed to the sheath portion of the stabilization glove. Of the two sheath fastener strips, one is affixed to the middle finger sheath and the to the ring finger sheath.

The modified support pillow provides for a support structure for the patient's arm that can be removably engaged to a complementary stabilization component. The complementary stabilization component for the present invention is the stabilization glove. This support pillow is a traditional pillow with an elongated body having a waterproof inner portion and fabric outer cover. One end of the out cover can be sealed and unsealed in order to insert or remove the inner portion. The opposing sides of the outer cover's opening have opposing Velcro® fasteners, allowing the opening to be selectively sealed and unsealed.

Towards the end of the support pillow opposite the outer cover opening, a plurality of Velcro® fasteners are permanently affixed to its top surface. More particularly, five (5) elongated hook component fastener strips, oriented such that their elongated bodies are parallel to each other and perpendicular to the elongated body of the support pillow comprise this plurality of Velcro® fasteners. As a result, when the stabilization glove contacts the portion of the support pillow where the Velcro fasteners are, the loop component strips from the stabilization glove engage the hook component strips of the support pillow. This engagement creates the removable attachment that provides for the device's stabilization function without physically restraining the patient in an inappropriate or undesirable manner.

When in use by a patient receiving hemodialysis, the support and stabilization device is complementary to the typical setting involving a comfortable chair. The support pillow can be placed near the patient's thigh and the armrest of the chair and oriented to the patient's target arm fits comfortably on it. The stabilization glove is placed on the hand of the target arm such that said arm will rest comfortably on the support pillow. The primary purpose of the stabilization glove is to provide a means for removably engaging a support component such that inadvertent or unconscious movement can be substantially resisted. The support component of the present invention is the support pillow. Thus, when a patient wearing the stabilization glove rests his arm (with the stabilization glove on it) on the support pillow in a manner that allows the opposing fasteners of the support pillow and stabilization glove to touch, these opposing fasteners engage to provide stability to the patient's arm. While this stability is sufficient to largely prevent inadvertent arm movement, it allows for deliberate and conscious movement by the patient. While the preferred embodiment contemplates that the patient will use the stabilization glove with the palm of the hand in contact with the support pillow, an alternate embodiment allows for the patient to have its palm up by having the loop fasteners on the stabilization glove on the dorsal side of the hand.

It is an object of this invention to provide a device that provides stability to the arm of a patient receiving dialysis treatment to prevent inadvertent or unconscious arm movement.

It is another object of this invention to provide said stability without physically restraining the patient so that the patient can still make conscious and deliberate movements.

It is yet another object of this invention to provide a device which supports the arm of a patient receiving dialysis treatment so that it can rest naturally and comfortably.

And yet another object of this invention is to provide a support and stabilization device that can be cleaned and sterilized in an effective and convenient manner.

These and other objects will be apparent to one of skill in the art.

BRIEF DESCRIPTION OF THE DRAWINGS

FIG. 1 is a top elevational view of the palm of a modified stabilization glove built in accordance with the preferred embodiment of the present invention.

FIG. 2 is a top elevational view of a modified support pillow built in accordance with the preferred embodiment of the present invention.

DETAILED DESCRIPTION OF THE INVENTION

Figure 3:
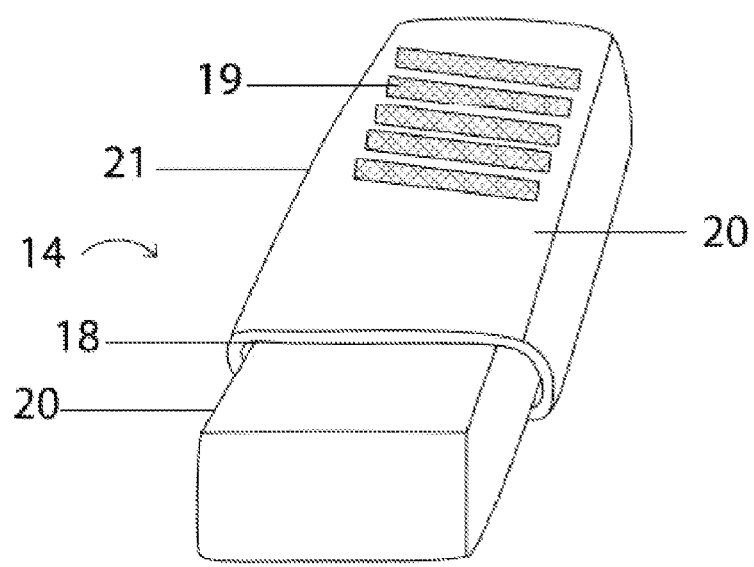
FIG. 3 is a perspective view of the modified support pillow with its cover partially removed.

Referring now to the drawings and in particular FIG. 1, a modified stabilization glove 10 is shown as a conventional glove 11 hand covering having separate sheaths for each finger and the thumb. The modified stabilization glove 10 is defined by the presence of a plurality of fabric hook-and-loop fastener components attached on the side of the stabilization glove 10 that covers the palmar surface of the hand (or the "palmar side" of the stabilization glove 10). Specifically, the stabilization glove 10 comprises two (2) loop component palm strips 12 permanently affixed to the palm section (on the palmar side) of the stabilization glove 10 and two (2) loop component finger strips 13 permanently affixed to the sheath portion (on the palmar side) of the stabilization glove 10. Regarding the two (2) finger strips 13, one is affixed to the middle finger sheath of stabilization glove 10 and the other is affixed to the ring finger sheath of stabilization glove 10.

The loop component strips on the stabilization glove 10 allow it to be removably attached to opposing hook component strips. In the preferred embodiment of the present invention, Velcro® strips are used for hook-and-loop fasteners. The stabilization glove 10 is constructed out of a fabric material and the palm strips 12 and finger strips 13 are sewn to the stabilization glove 10 at their locations to be permanently affixed to the stabilization glove 10. The fabric material used to construct the stabilization glove 10 additionally allows it to also assist in keeping the hand of user of the stabilization glove 10 warm.

Referring now to FIGS. 2 and 3, a modified support pillow 14 is shown as a traditional pillow structure 15 having an elongated body with a proximal end 16 and a distal end 17. The proximal end 16 is defined by a sealable opening 18 that extends along the length of the proximal end 16. Permanently affixed to the top surface of the support pillow 14 towards the distal end 17 are five (5) hook-and-loop fastener components. These hook-and-loop fastener components comprise five (5) hook component strips 19 oriented such that their elongated bodies are parallel to each other and perpendicular to the elongated body of the support pillow 14. These hook component strips 19 on the support pillow 14 can removably engage with the loop component strips of the stabilization glove 10, allowing the stabilization glove 10 to be removably attached to the support pillow 14. As with the stabilization glove 10, Velcro® strips are used for hook-and-loop fastener components on the support pillow 14 in the preferred embodiment of the present invention.

The support pillow 14 has two primary structural components, an inner pillow 20 and an outer cover 21. The inner pillow 20 is a modified conventional stuffed pillow having the elongated shape of the support pillow 14 and pillow stuffing enclosed in an exterior casing. The inner pillow 20 is modified in that this exterior casing is a waterproof. The outer cover 21 is a fabric material, where said material is selected for comfort against the skin as well as for efficacy and ease of cleaning and sterilization. The outer cover 21 houses the sealable opening 18 of the modified pillow 14 such that assembly of support pillow 14 comprises inserting the inner pillow 20 into the outer cover 21 through the sealable opening 18 when the sealable opening 18 is held open. Once the inner pillow 20 is completely inside the outer cover 21 the sealable opening 18 is sealed and assembly is complete.

The sealable opening 18 is defined by opposing hook-and-loop fasteners which when pressed together, engage and attach to each other to cause the sealable opening 18 to be sealed. Opposing Velcro® strips, which are permanently affixed to the opposing ends of the sealable opening 18, are used for the opposing hook-and-loop fasteners at the sealable opening 18. If it is desired to clean, wash, or sterilize the support pillow 14, the inner pillow 20 is first removed by unsealing the sealable opening 18 and pulling the inner pillow out. Then, the outer cover 21 can be cleaned, washed, or sterilized. Once this process is complete, the support pillow 14 can be reassembled and the support pillow 14 is again ready to be used.

Figure 4:
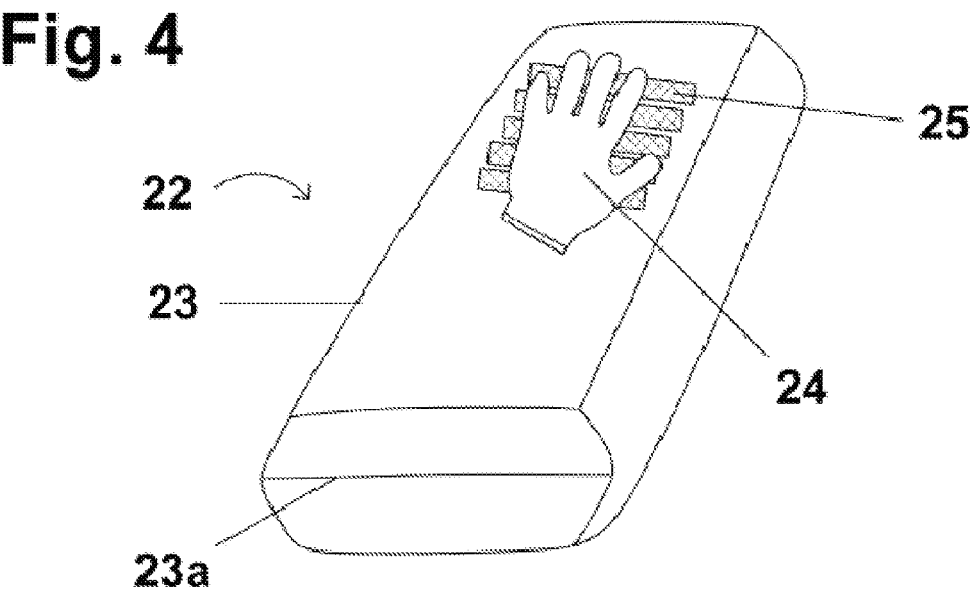
FIG. 4 is a perspective view of the modified stabilization glove attached to the modified support pillow.

Referring now to FIG. 4, the components of the support and stabilization device 22 are show together. As previously discussed, the components of the support and stabilization device 22 are the support pillow 23, shown with its sealable opening 23a visible, and the stabilization glove 24. When the stabilization glove 24 is attached to the support pillow 23, they work in concert to support and stabilize the arm of a dialysis patient. This is accomplished because when the loop fastener components on the stabilization glove 24 contact the hook fastener components 25 on the support pillow 23, these fastener components attach to one another and hold the stabilization glove 24 and support pillow 23, along with the arm of a patient whose hand is inside the stabilization glove 24, together. Because of the nature of hook-and-loop fasteners, and more particularly Velcro® strips, this attachment does not create an actual, physical restraint on the patient's arm. The attachment between the can be broken at any time with simply deliberate and conscious action by the patient. This attachment, however, does allow the support and stabilization device 22 to prevent inadvertent or accidental movement of the patient's arm that is receiving dialysis treatment. Thus, it is able to provide the desired stabilization without subjecting the patient to any undesired or inappropriate physical restraint.

Figure 5:
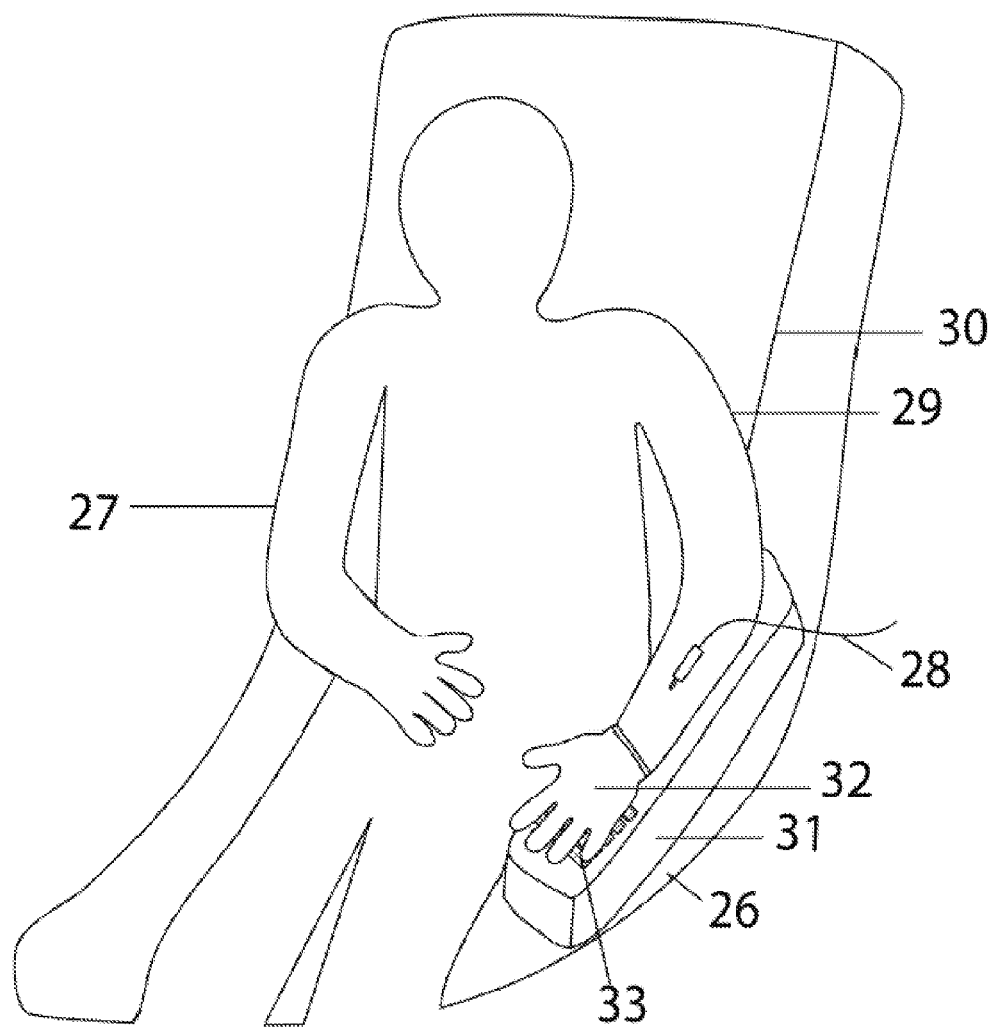
FIG. 5 is a perspective view of a patient receiving dialysis utilizing a support and stabilization device built in accordance with the preferred embodiment of the present invention.

Referring now to FIG. 5, the support and stabilization device 26 is shown being used by a patient 27 receiving hemodialysis. This dialysis treatment typically requires the patient's 27 blood to be accessed by certain input/output medical components 28 through the patient's arm 29. The patient 27 will often be seated in a chair 30. The support and stabilization device 26 allows the target arm 29 rest on the support pillow 31. The stabilization glove 32 is placed on the hand of the target arm 29 and is intended to come to rest on top of the hook component strips 33 of the support pillow 31. When contacting the hook component strips 33, the loop component strips on the stabilization glove 32 engage the hook component strips 33 and cause the stabilization glove 32 to become removably attached to the support pillow 31.

Figure 6:
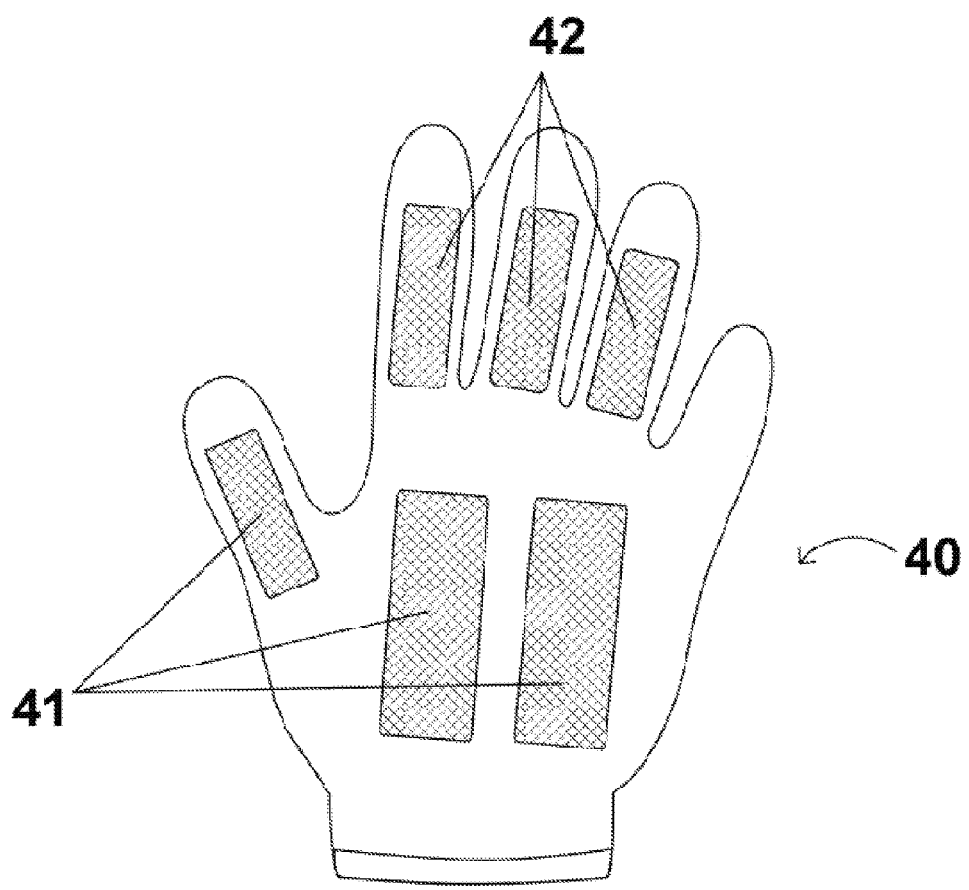
FIG. 6 is a top elevational view of a modified stabilization glove built in accordance with an alternate embodiment of the present invention.

Referring now to FIG. 6, an alternate embodiment of a stabilization glove 40 built in accordance with the present invention is shown. This stabilization glove 40 is distinct from that of the preferred embodiment in that the plurality of hook-and-loop fastener components are attached on the side of the stabilization glove 40 that covers the dorsal surface of the hand (or the "dorsal side" of the glove). Specifically, this stabilization glove 40 comprises three (3) loop component opisthenar strips 41 permanently affixed to the area of the stabilization glove 40 covering the opisthenar of the hand (the "palm section" on the dorsal side of the glove) and three (3) loop component phalange strips 42 permanently affixed to the sheath portion of the stabilization glove 40 on the opisthenar side of the hand. Regarding the three (3) phalange strips 42, one is affixed to the index finger sheath, middle finger sheath, and ring finger sheath of stabilization glove 40 (on the dorsal side of the glove). This alternate embodiment of the stabilization glove 40 allows a patient to stabilize the arm receiving treatment with the patient's palm up, which may be more comfortable for some patients.

It is further contemplated that the instant invention may be used in protocols beyond hemodialysis. Specifically, its utilization extends to other applications where a patient is receiving treatment that requires or where it is desirable for the arm of the patient to be supported and kept substantially still without the use of a physical restraint.

The instant invention has been shown and described herein in what is considered to be the most practical and preferred embodiments. It is recognized, however, that variations and departures may be made therefrom within the scope of the inventions and that obvious modifications will occur to a person of ordinary skill in the art.

What is claimed is:

1. A support and stabilization device for use by a patient desiring of arm stabilization without the use of a physical restraint comprising:
   a support pillow having at least one pillow fastener portions permanently affixed to the exterior of said support pillow;
   a stabilization hand covering having a palmar side, a dorsal side, a finger cover area, and a palm cover area, wherein said stabilization hand covering is adapted to be placed over a wearer's hand sufficient to cover at least a portion of the wearer's hand and has a plurality of discrete glove fastener portions permanently affixed to the exterior of the stabilization hand covering, positioned on both the finger cover area and palm cover area on either the palmar side or dorsal side, said glove fastener portions each defining a strip of glove fastening material that is capable of engaging said pillow fastener portions to form a removable attachment; and
   wherein said pillow fastener portions and said glove fastener portions configure the support pillow and stabilization hand covering to enable a wearer's hand covered by the stabilization hand covering to be selectively attached to the support pillow sufficiently to resist inadvertent or unconscious movement of the attached hand and arm associated therewith as well as to be selectively detached from the support pillow through deliberate movement of the attached hand or associated arm.

2. The device of claim 1, wherein said support pillow has an elongated body with a proximal pillow end and a distal pillow end, wherein said pillow fastener portions are positioned on the exterior of the outer pillow cover of the support pillow on the distal pillow end.

3. The device of claim 2, wherein said support pillow comprises an outer pillow cover and an inner pillow portion, wherein said inner pillow portion is designed to be fully enclosed in outer pillow cover.

4. The device of claim 3, wherein the outer pillow cover includes a sealable opening, wherein said sealable opening comprises an aperture in the outer pillow cover sized to allow the inner pillow portion to pass through in the outer pillow cover and at least one fastener capable of causing the sealable opening to be selectively closed such that the aperture is no longer sized to allow the inner pillow portion to pass through in the outer pillow cover.

5. The device of claim 1, wherein said pillow fastener portions comprise at least one strip of a hook-and-loop fastener component.

6. The device of claim 1, wherein said finger cover area is adapted to cover at least one finger of the wearer's hand and the palm cover area is adapted to cover the palm areas of the wearer's hand, wherein the finger cover area includes a plurality of distinct glove fastener portions and the palm cover area includes at least one distinct glove fastener portions.

7. The device of claim 1, wherein said stabilization hand covering comprises a modified glove, with the finger cover area defined by at least one sheath.

8. The device of claim 7, wherein said glove fastener portions are affixed to the palmar side of the modified glove.

9. The device of claim 7, wherein said glove fastener portions are affixed to the dorsal side of the modified glove.

10. The device of claim 7, wherein said glove fastening material defines a hook-and-loop fastener component.

11. The device of claim 7, wherein the at least one sheath on the modified glove includes at least one of said glove fastener portions and the palm section of said modified glove includes a plurality of said glove fastener portions.

12. The device of claim 7, wherein a plurality of sheaths on the modified glove each include discrete glove fastener portions and the palm section of the modified glove includes at least one of said glove fastener portions.

13. A support and stabilization device for use by a patient desiring of arm stabilization without the use of a physical restraint, comprising:
   a support pillow having at least one pillow fastener portions permanently affixed to the exterior of said support pillow;

a stabilization glove having a palmar side, a dorsal side, a plurality of sheaths, and a palm cover area, wherein said stabilization glove is adapted to be placed over a wearer's hand;

a plurality of discrete glove fastener portions permanently affixed to the exterior of either its palmar side or its dorsal side such that each sheath includes at least one glove fastener portion and the palm section of the modified glove includes multiple distinct glove fastener portions, wherein said glove fastener portions are capable of engaging said pillow fastener portions to form a removable attachment; and wherein said pillow fastener portions and said glove fastener portions configure the support pillow and stabilization glove to enable a wearer's hand covered by the stabilization glove to be selectively attached to the support pillow sufficiently to resist inadvertent or unconscious movement of the attached hand and arm associated therewith as well as to be selectively detached from the support pillow through deliberate movement of the attached hand or associated arm.

14. A support and stabilization device for use by a patient desiring of arm stabilization without the use of a physical restraint, comprising:

a support pillow having at least one pillow fastener portions permanently affixed to the exterior of said support pillow, said support pillow having an elongated body with a proximal pillow end and a distal pillow end, said support pillow comprising an outer pillow cover and an inner pillow portion wherein said inner pillow portion is designed to be fully enclosed in outer pillow cover, wherein said pillow fastener portions are positioned on the exterior of the outer pillow cover of the support pillow on the distal pillow end;

wherein the outer pillow cover includes a sealable opening, wherein said sealable opening comprises an aperture in the outer pillow cover sized to allow the inner pillow portion to pass through in the outer pillow cover and at least one fastener capable of causing the sealable opening to be selectively closed such that the aperture is no longer sized to allow the inner pillow portion to pass through in the outer pillow cover;

wherein said pillow fastener portions comprise at least one strips of a hook-and-loop fastener component;

a stabilization hand covering comprising a modified glove having a palmar side, said modified glove including a plurality of discrete glove fastener portions permanently affixed to the palmar side its exterior, said glove fastener portions each defining a strip of a hook-and-loop fastener component capable of engaging said pillow fastener portions to form a removable attachment;

wherein each sheath on the modified glove includes at least one of said glove fastener portions and the palm section of said modified glove includes at least one of said glove fastener portions; and wherein said pillow fastener portions and said glove fastener portions configure said support pillow and said stabilization hand covering to enable the hand of a patient wearing the modified glove to be removably attached to the support pillow sufficiently to resist inadvertent or unconscious movement of the attached hand and arm associated therewith as well as to be selectively detached from the support pillow through deliberate movement of the attached hand or associated arm.

* * * * *